United States Patent [19]

Lutz

[11] Patent Number: 4,528,416
[45] Date of Patent: Jul. 9, 1985

[54] ETHYLENE OLIGOMERIZATION PROCESS CARRIED OUT IN A MONOHYDRIC/DIHYDRIC ALCOHOL SOLVENT MIXTURE

[75] Inventor: Eugene F. Lutz, Houston, Tex.

[73] Assignee: Shell Oil Company, Houston, Tex.

[21] Appl. No.: 658,949

[22] Filed: Oct. 9, 1984

[51] Int. Cl.³ .............................................. C07C 3/21
[52] U.S. Cl. ................................ 585/527; 585/510; 585/514; 585/523
[58] Field of Search ............... 585/527, 510, 514, 523

[56] References Cited

U.S. PATENT DOCUMENTS

| | | | |
|---|---|---|---|
| 3,647,914 | 3/1972 | Glockner et al. | 585/520 |
| 3,647,915 | 3/1972 | Bauer et al. | 585/523 |
| 3,676,523 | 7/1972 | Mason | 585/523 |
| 3,686,351 | 8/1972 | Mason | 585/523 |
| 3,737,475 | 6/1973 | Mason | 585/523 |
| 3,825,615 | 7/1974 | Lutz | 585/527 |
| 4,020,121 | 4/1977 | Kister et al. | 585/520 |
| 4,260,844 | 4/1981 | O'Donnell et al. | 585/525 |
| 4,288,648 | 9/1981 | Beach et al. | 585/523 |
| 4,382,153 | 5/1983 | Beach et al. | 585/527 |
| 4,482,640 | 11/1984 | Knudsen et al. | 585/523 |

FOREIGN PATENT DOCUMENTS 1164855  9/1969  United Kingdom ............... 585/523

*Primary Examiner*—D. E. Gantz
*Assistant Examiner*—A. Pal

[57] ABSTRACT

An improved process for the conversion of ethylene to its linear alpha-olefin oligomers by contact with a catalytic nickel complex dissolved in a polar organic solvent. The improvement relates to the use as solvent in such a process of a mixture of certain monohydric and dihydric alcohols in specified proportions. Practice of the invention provides enhanced rate of ethylene oligomerization and/or modification of the carbon number distribution of the product oligomer mixture.

28 Claims, No Drawings

4,528,416

ETHYLENE OLIGOMERIZATION PROCESS CARRIED OUT IN A MONOHYDRIC/DIHYDRIC ALCOHOL SOLVENT MIXTURE

BACKGROUND OF THE INVENTION

This invention relates to an improvement in a process for the production of the linear alpha-olefin oligomers of ethylene. More particularly, this invention is directed to an improvement in a process for the conversion of ethylene to oligomers by contact with a catalytic nickel complex dissolved in a polar organic solvent.

Linear mono-olefins are compounds having established utility in a variety of applications. For example, linear mono-olefins having carbon numbers in of about 8 to 20 are known to be particularly useful as intermediates in the production of surfactants, lubricants and plasticizers.

It is known in the prior art to prepare linear mono-olefins by oligomerizing ethylene at elevated temperature and pressure in a polar reaction solvent containing a catalytic nickel complex. Particularly useful as catalysts for this service are the complexes prepared as the reaction product of an olefinic nickel compound and a bidentate ligand. The olefinic nickel compound is suitably a reduced nickel compound or a $\pi$-alkyl nickel compound. The art expresses preference for use as reaction solvent in such a process of a dihydric alcohol solvent, particularly an aliphatic diol of 2 to 7 carbon atoms. Illustrative ethylene oligomerization processes employing a nickel complex catalyst and a polar solvent are described in: U.S. Pat. No. 3,676,523, U.S. Pat. No. 3,686,351, and U.S. Pat. No. 3,737,475, all to R. F. Mason; U.S. Pat. No. 3,644,564 to Van Zwet et al; U.S. Pat. No. 3,647,914 to Glockner et al; U.S. Pat. No. 3,647,915 to Bauer et al; and U.S. Pat. No. 3,825,615 to E. F. Lutz; U.S. Pat. No. 4,020,121 to A. T. Kister et al, and U.S. Pat. No. 4,260,844 to O'Donnell et al.

The present invention centers on the use for one such oligomerization process of a reaction solvent which comprises a specific combination of both monohydric and dihydric alcohol components. There are disclosures in the above-referenced patents of the use of various monohydric alcohols as solvents for the subject process. Use of monohydric alkanols has, however, been considered to have disadvantage in such a process, when compared to the performance of dihydric alcohols, for instance, from the standpoint of the rate of ethylene oligomerization. A clear preference has existed for the use of process solvents in this service which consist essentially of the dihydric alcohols.

SUMMARY OF THE INVENTION

The present invention is directed to an improvement in the conventional process for the oligomerization of ethylene in the presence of a nickel chelate catalyst and in a polar reaction solvent. According to the invention, the ethylene reactant is contacted with the catalyst in a mixed reaction solvent which comprises both a lower aliphatic dihydric alcohol component and a lower aliphatic monohydric alcohol component.

In one aspect, the invention relates to the discovery that such use of a reaction solvent mixture results in improvement in the rate of ethylene oligomerization and/or modification of the carbon number distribution of the product oligomer mixture. In other aspects the invention relates to the finding that desirable results in this regard are critically dependent upon several processing conditions. Of particular importance is a requirement that the solvent combine the monohydric and dihydric alcohol components only in critically limited relative proportions. For purposes of the invention, the solvent mixture necessarily contains between about 40 and 82 percent by weight of the aliphatic dihydric alcohol(s) and between about 18 and 60 percent by weight of the aliphatic monohydric alcohol(s), calculated on the combined weight of these two components in the solvent. Further critical to the process of this invention is operation at an ethylene partial pressure of at least about 800 psig. Oligomerization processes in which either the solvent contains proportions of the monohydric and dihydric alcohol components outside of the specified weight ranges or the ethylene partial pressure is less than about 800 psig do not result in any significant degree of reaction modification with respect to either the rate of oligomer formation or product oligomer carbon number distribution. Several other processing conditions have additionally be observed to contribute to obtaining full advantage of the benefits associated with the use of a dihydric alcohol and monohydric alcohol reaction solvent mixture.

Accordingly, the invention is summarily described as an improvement in a process for the preparation of oligomers of ethylene which comprises reacting ethylene in a polar solvent and in the presence of a catalyst which is a chelate of nickel with a bidentate ligand. The improvement is particularly directed to such an oligomerization reaction carried out at a temperature of at least about 85° C. and under a partial pressure of ethylene of at least about 800 psig in a solvent mixture which comprises between about 40 and 82 percent by weight of one or more lower aliphatic dihydric alcohols and between about 18 and 60 percent by weight of one or more lower aliphatic monohydric alcohols, said percentages by weight being calculated on the total weight of the dihydric alcohol(s) and monohydric alcohol(s) in the solvent.

DESCRIPTION OF THE PREFERRED EMBODIMENTS

The improved process of this invention is broadly applicable to processes employing a nickel complex catalyst to promote ethylene oligomerization in a polar reaction solvent.

Oligomers are addition products which contain two or more of the monomer units (in this case, two or more ethylene units), but not as many units as the relatively high molecular weight addition products which are referred to as polymers. The present invention is particularly adapted for the production of linear mono-olefinic oligomers of ethylene containing from 2 to about 20 monomer units (i.e., from 4 to about 40 carbon atoms).

Catalysts suitable for use in the invention are complexes of nickel comprising an atom of nickel chelated with a bidentate chelating ligand. Such catalysts are typically prepared by reacting a suitable bidentate ligand either with an olefinic nickel compound such as bis(cyclooctadiene) nickel (O) or a $\pi$-allyl nickel compound, or more preferably, with a simple divalent nickel salt and a reducing agent, e.g., boron hydride, in the presence of ethylene and in a suitable polar organic solvent. Preparation and use of catalysts of the former type are described in U.S. Pat. No. 3,644,564 to Van Zwet et al, U.S. Pat. No. 3,647,914 to Glockner et al, and U.S. Pat. No. 3,647,415 to Bauer et al. Preparation and use of catalysts of the latter type are described in U.S. Pat No. 3,676,523, No. 3,686,351, and No. 3,737,475, all to R. F. Mason, as well as U.S. Pat. No. 3,825,615 to E. F. Lutz. The disclosures of all of these said patents with respect to the components, preparation, and use of such catalysts are incorporated herein by reference.

A notable feature of each such ethylene oligomerization process catalyzed by a chelate of nickel with a bidentate ligand, is a product mixture in which the several oligomers have a characteristic carbon number distribution. The aforementioned patents, for example, describe a distribution pattern for the individual olefinic oligomers in any given product which is in a geometric form and can be approximated by a single constant, referred to as the "product distribution constant" or "K factor", according to the mathematical expression:

$$K = \frac{\text{mols of } C_{n+2} \text{ olefin}}{\text{mols of } C_n \text{ olefin}} ; \text{(for } n = 4, 6, 8 \ldots \text{)}.$$

A relatively high K factor, e.g., on the order of about 0.75 to 0.85, is often desirable to maximize the production of olefins in the carbon number range of about $C_{10}$ to $C_{20}$. It is known that the product distribution constant can be influenced by a number of factors, including the type of bidentate ligand, the concentration of catalyst in the solvent, the degree of ethylene saturation in the reaction solution, the type of reaction solvent, and the reaction conditions.

Preferred bidentate chelating ligands for catalysts useful in the invention are known to include those having a tertiary organophosphorous moiety with a suitable functional group substituted on a carbon atom attached directly to, or separated by no more than two carbon atoms from, the phosphorous atom of the organophosphorous moiety. Representative ligands of this type are the compounds

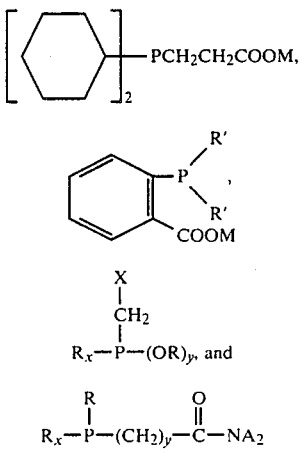

wherein R (independently in each occurrence) represents a monovalent organo group, R' (independently in each occurrence) represents a monovalent hydrocarbyl group, X is carboxymethyl or carboxyethyl, A is hydrogen or a monovalent organo group, M is an alkali metal (preferably sodium or potassium), and x and y (independently) are each either zero, one, or two and the sum of x and y is two, with the proviso that when x is two, the R groups may, together with the phosphorus atoms, form a mono or bicyclic heterocyclic phosphine having from 5 to 7 carbon atoms in each ring thereof. Particularly preferred complexes are those described in U.S. Pat. No. 3,676,523 in which the ligand is an o-dihydrocarbylphosphinobenzoic acid or its alkali metal salt and most preferably p-diphenylphosphinobenzoic acid; in other preferred complexes described in U.S. Pat. No. 3,825,615, the ligand is dicyclohexylphosphinoproponic acid or its alkali metal salt.

Although it is not desired to be bound by any particular theory, it has been suggested that the catalyst molecule undergoes chemical transformation during the course of the oligomerization reaction, possibly involving coordination and/or bonding of ethylene to the nickel moiety. However, the bidentate chelating ligand apparently remains complexed and/or chemically bonded to the nickel moiety during the course of the oligomerization reaction and this complex of the nickel and the chelating ligand is then the effective catalytic species of the oligomerization process. In any event, the bidentate ligand, such as the phosphorus-containing chelating ligand, is considered an essential component of the catalyst and, provided the nickel catalyst contains the required bidentate ligand, the nickel catalyst may be complexed with a variety of additional organic complexing ligands.

As is the case in prior art practice with such nickel chelate catalysts, the molar ratio of nickel to bidentate ligand used in catalyst preparation is preferably at least 1:1, i.e., the nickel is present in equimolar amount or in molar excess. In the preparation of catalyst complexes from a nickel salt, a ligand and a reducing agent, the molar ratio of nickel salt to ligand is suitably in the range from 0.8:1 to 5:1 with molar ratios of about 1.0:1 to 3:1 preferred and ratios of about 1:1 especially suitable. In these preparations, the reducing agent such as boron hydride is suitably present in equimolar amount or molar excess relative to the nickel salt. For economic reasons, it is preferred that the reducing agent/nickel ratio not exceed about 15:1. More preferably, this ratio is between about 1:1 and about 10:1, while a ratio of about 2:1 is considered particularly preferred. Ratios somewhat below 1:1 are also suitable.

The nickel complex catalysts are suitably performed by contacting the catalyst precursors in the presence of ethylene in a suitable polar organic diluent or solvent, which is not reduced by the (boron hydride) reducing agent. In a preferred modification of producing the preferred catalyst complexes as detailed in the patents to Mason and Lutz, supra, the solvent, nickel salt and ligand are contacted in the presence of ethylene before the addition of reducing agent. It is essentially that such catalyst compositions be prepared in the presence of ethylene. The catalysts are suitably prepared at temperatures of about 0° to 50° C., with substantially ambient temperatures e.g., 10°–30° C. preferred. The ethylene pressure and contacting conditions should be sufficient to substantially saturate the catalyst solution. For example, ethylene pressures may be in the range from 10 to 1,500 psig or higher. Substantially elevated ethylene pressure, e.g., in the range from 400 to 1,500 psig are preferred.

The ethylene oligomerization process of the invention is necessarily carried out in a solvent which, for purposes of the particular improvement of the invention, comprises both an aliphatic dihydric alcohol ("diol") component and an aliphatic monohydric alcohol ("alkanol") component. The diol is suitably a lower diol, preferably one selected from the group consisting of $C_2$ to $C_7$ aliphatic diols and mixtures thereof. These suitable diols include, for example, both the vicinal alkane diols such as ethylene glycol, propylene glycol, 2-methyl-1,2-propanediol, 1,2-butanediol and 2,3-butanediol, and the alpha-omega alkane diols such as 1,3-propanediol 1,4-butanediol, 1,5-pentanediol, 1,6-hexanediol, and 1,7-heptanediol. Alpha-omega diols of 4 to 6 carbon atoms are preferred solvents with 1,4-butanediol being particularly preferred. Mixtures of such diols are very suitable for use as the aliphatic dihydric alcohol component of the reaction solvent for purposes of the invention.

The alkanol component is suitably a lower alkanol, preferably one selected from the group consisting of $C_2$ to $C_7$ aliphatic monohydric alcohols and mixtures thereof. The alkanol is preferably either primary or secondary; the presence of tertiary alkanols in the solvent mixture has not been found to be responsible for process rate enhancement, although they are usefully applied to modify the product K-factor. Examples of suitable alkanols include ethyl alcohol, n-propyl alcohol, isopropyl alcohol, n-butyl alcohol, isobutyl alcohol, sec.-butyl alcohol tert-butyl alcohol, n-pentyl alcohol, isopentyl alcohol, tert-pentyl alcohol, amyl alcohol, 2-methyl-2-butanol, 3-methyl-2-butanol, n-hexanol, isohexanol, and 2-ethyl-1-hexanol, etc. The primary $C_2$ to $C_5$ alkanols are considered most preferred for use in the invention, particularly n-propanol, n-butanol and n-pentanol.

The alkanol solvent components are readily soluble in the suitable diols and the resulting mixture is compatible with other components of the oligomerization process mixture.

In its broader aspects, the invention centers upon modifications in process performance provided by the mixed alkanol and diol solvent system. The lower alkanol and the lower diol in the oligomerization solvent are observed to have a synergistic influence upon process performance (by increasing reaction rate and/or product K-factor) over a critical range of relative properties. Suitable proportions may be conveniently stated in terms of a concentration of alkanol in the solvent which is between about 18 and 60 percent by weight (%w), calculated on total weight of the specified alkanol and diol components present in the solvent, with the diol then making up the remaining 40 to 82%w. The use of either lesser or greater quantities of alkanol, that is, concentrations below or above this 18 to 60%w range, do not result in either a significant increase in reaction rate or K-factor, compared to performance with alkanol or diol alone as solvent. As a general rule, solvents comprising between about 20 and 45%w alkanol, relative to total alkanol and diol are preferred from the standpoint of increasing oligomerization reaction rate, while an alkanol concentration of between about 20 and 40%w is more preferred for this objective. Higher concentrations of alkanol, e.g., 35 to 60%w and particularly 40 to 55%w, do not generally provide significant increase in reaction rate and are preferred from the standpoint of their performance in increasing product K-factor. Overall, alkanol concentrations in the range from about 20 to 35%w are considered most preferred for their influence in combining a maximum increase in reaction rate (e.g., 10 to 20% or more) with a moderate increase in K-factor (e.g., 5 to 10%), compared to the performance of a process utilizing the alkanol or the diol alone as a solvent.

The alkanol and diol mixture constitutes the major fraction, preferably the predominant fraction, e.g., 80%w or more, of the total oligomerization solvent, with the remainder suitable made up of other substances which act in some respects as solvents for the ethylene reactant and the catalyst. A reaction solvent which consists essentially of the specified alkanol and diol components is considered most preferred. As the ethylene reactant is introduced into the process and as the oligomerization reaction proceeds, the solvent will, of course, contain substantial amounts of ethylene and of oligomerization products and by-products.

With exception of the utilization of the mixed alkanol and diol solvent and the criticalities observed for process pressure, the process of the invention may be practiced according to methods and under conditions well known in the prior art, for instance, as described in the above-referenced patents. Very suitably, a mixture of the catalyst and solvent is prepared and charged to an autoclave or similar pressure reactor. The catalyst is typically prepared in a solvent, which is preferably either a diol solvent or an alkanol and diol mixture as specified for purpose of the invention. Ethylene and solvent are introduced and the reaction mixture is maintained with agitation at the desired reaction temperature and pressure.

Process pressure has been found to be a critical aspect of the present invention. Improvements associated with the alkanol and diol solvent mixture are realized only for operation at ethylene partial pressures in excess of about 800 psig. At lower pressures, the specified alkanol and diol solvent mixture is not responsible for any meaningful effect upon either oligomerization reaction rate or oligomer product distribution. As a rule the degree of benefit realized from practice of the invention increases with increasing ethylene reactant partial pressure. Preference may be expressed for a process in which ethylene partial pressure is in the range from about 900 to 2000 psig, while practice in the range from about 1000 to 1800 psig is more preferred and practice in the range from about 1100 to 1500 psig is considered most preferred.

Although process temperature is not critical for purposes of the invention, the degree to which the mixed alkanol/diol solvent modifies the oligomerization reaction rate and/or K-factor is dependent upon the reaction temperature. For best overall results, process temperature is preferably at least about 80° C., more preferably at least about 85° C. (particularly between about 85° C. and 100° C.), and most preferably at least about 90° C. (particularly between about 90° C. and 105° C.).

Contact between ethylene and catalyst in the solvent and under suitable conditions of temperature and pressure is initiated and continued until the desired degree of oligomerization had occurred. The liquid product mixture is then suitably treated according to conventional procedures, typically including separation of an oligomer-rich liquid phase from the solvent phase, scrubbing of the oligomer-rich phase to remove residual catalyst, de-ethanization of the scrubbed liquid, and further work-up of the de-ethanized product to separate it into various product fractions. The above referenced patents and also U.S. Pat. No. 4,229,607 to C. R. Gum et al and U.S. Pat. No. 4,284,837 to E. F. Lutz describe suitable procedures for carrying out the several steps of the overall oligomerization process for purposes of the invention, in either a batch or a continuous manner.

The invention is further illustrated by reference to the following examples (according to the present invention) and comparative experiments (not according to the invention).

For each of the examples and comparative experiments, a solution of nickel complex catalyst was prepared by mixing solvent, $NiCl_2 \cdot 6H_2O$, o-diphenylphosphinobenzoic acid, KOH, and sodium borohydride in the presence of ethylene. In each case, addition was made to a 500 cc stirred round bottom flask under nitrogen atmosphere of about 301 grams of solvent (either a lower alkanol, i.e., n-propanol or n-butanol, or a lower alkane diol, i.e., 1,4-butanediol (1,4-BD), or an alkanol and alkane diol mixture), about 1.32 grams of a solution of $NiCl_2 \cdot 6H_2O$ in 1,4-BD (0.017 grams of Ni per gram of solution); about 8.11 grams of a solution of o-diphenylphosphinobenzoic acid in 1,4-BD (0.0128 grams of ligand per gram of solution), and about 2.24 grams of a solution of KOH in 1,4-BD (0.00905 grams of KOH per gram of solution). The resulting clear yellow mixture contains 67–76 ppm nickel, 328–244 ppm ligand, and had molar ratios of nickel to ligand of 1.02–1.18, of sodium borohydride to nickel of 1.17–1.45, and of potassium hydroxide to ligand of 0.98 to 1.06.

The mixture was pressured into a one-liter autoclave, together with 35 grams of ethylene, and stirred for 30 minutes. To the autoclave was then added a solution containing about 0.0227 grams of sodium borohydride in 0.400 grams of 1,4-BD and 0.400 grams of water, followed by a further 2.47 grams of butanediol and 87.5 grams of ethylene.

The autoclave was rapidly heated to the desired temperature (either 85° C. or 95° C.) to initiate the oligomerization reaction, and maintained at this temperature for the full reaction period. Ethylene was introduced to maintain desired pressure, e.g., about 1320 psig or about 910 psig or about 720 psig. Samples of the reaction mixture were taken after 60 grams of ethylene uptake, and in some cases also after 136 grams of ethylene uptake, for determination of K factors.

EXAMPLES 1–4

Following the specified procedures, four examples were carried out utilizing as reaction solvent a mixture of 1,4-butanediol with a lower primary alkanol (n-propanol in Example 1 and n-butanol in Examples 2–4). The oligomerization reaction mixtures contained about 76%w 1,4-butanediol and 24%w alkanol, calculated on total weight of diol and alkanol. Each of the examples was conducted under a pressure of about 1320 psig.

Results in terms of K-factor and reaction rate are reported in Table 1, together with the results of five comparative experiments (designated A–E). The comparative experiments were carried out under the same conditions and procedures, but utilizing reaction solvents not in accordance with the invention. Reaction rate reported is the maximum during the course of the run and is in terms of the grams of ethylene uptake per liter of catalyst solution per hour.

TABLE 1

| | Solvent[1] | | Maximum | K-factor | |
|---|---|---|---|---|---|
| | Alkanol | Diol | Reaction Rate | Intermediate[2] | Final[3] |
| Example No. | | | | | |
| 1 | 24% w n-P | 76% w 1,4-BD | 479 | 0.80 | 0.76 |
| 2 | 24% w n-B | 76% w 1,4-BD | 467 | 0.82 | 0.78 |
| 3 | 24% w n-B | 76% w 1,4-BD | 475 | 0.82 | 0.78 |
| 4 | 24% w n-B | 76% w 1,4-BD | 469 | 0.84 | 0.80 |
| Comparative Experiment | | | | | |
| A | | 100% w 1,4-BD | 378 | 0.73 | 0.68 |
| B | | 100% w 1,4-BD | 360 | 0.71 | 0.67 |
| C | | 100% w 1,4-BD | 375 | 0.73 | 0.69 |
| D | 14% w n-B | 86% w 1,4-BD | 316 | 0.72 | 0.66 |
| E | 100% w n-P | | 138 | 0.68 | |

[1] n-P represents n-propanol and n-B represents n-butanol.
[2] Determined after 60 grams of ethylene uptake.
[3] Determined after 136 grams of ethylene uptake.

EXAMPLES 5–7

Three examples were carried out under the above-described procedures, utilizing as solvent a mixture of 24%w n-butanol (n-B) and 76%w, 1,4-butanediol. Process pressure in each case was about 910 psig. Results for Examples 5–7 are presented in Table 2, together with the results of four comparative experiments (F–I) carried out in a 1,4-butanediol solvent, without the lower alkanol.

TABLE 2

| | Solvent[1] | | Maximum | K-factor | |
|---|---|---|---|---|---|
| | Alkanol | Diol | Reaction Rate | Intermediate[2] | Final[3] |
| Example No. | | | | | |
| 5 | 24% w n-B | 76% w 1,4-BD | 250 | 0.75 | |
| 6 | 24% w n-B | 76% w 1,4-BD | 290 | 0.74 | 0.69 |
| 7 | 24% w n-B | 76% w 1,4-BD | 268 | 0.75 | |
| Comparative Experiment | | | | | |
| F | | 100% w 1,4-BD | 389 | 0.63 | 0.58 |
| G | | 100% w 1,4-BD | 302 | 0.67 | |
| H | | 100% w 1,4-BD | 388 | 0.67 | 0.64 |
| I | | 100% w 1,4-BD | 331 | 0.70 | 0.66 |

Table 2 illustrates practice of the invention under conditions of pressure which result in an increase in K-factor, but not reaction rate, relative to the comparative examples utilizing only a butanediol solvent.

EXAMPLES 8-9

Table 3 presents the results of two examples and one comparative experiment run at a temperature of 85° C. and at pressures in the range from 944–956 psig. The molar ratio of sodium borohydride to nickel used in catalyst preparation for these runs was in the range from 1.50 to 1.58.

TABLE 3

| | Solvent[1] | | Maximum | K-factor | |
| --- | --- | --- | --- | --- | --- |
| | Alkanol | Diol | Reaction Rate | Intermediate[2] | Final[3] |
| Example No. | | | | | |
| 8 | 24% w n-B | 76% w 1,4-BD | 230 | 0.79 | 0.70 |
| 9 | 48% w n-B | 52% w 1,4-BD | 168 | 0.88 | 0.77 |
| Comparative Experiment | | | | | |
| J | 14% w n-B | 86% w 1,4-BD | 233 | 0.69 | 0.64 |

Although neither of examples 8 and 9 according to the invention exhibit increased reaction rate at the temperature (85° C.) and pressure (about 950 psig) of these runs, both show significant increases in product K-factors over those of comparative example J.

Summary of Pressure Effects

Table 4 presents in summary form the results of several examples and comparative examples to illustrate the critical effect of process pressure upon both maximum reaction rate and K-factor. Except as noted, the reaction rate and K-factor results reported are the averages of several representative runs. The Table illustrates that at a pressure of about 1320 psig, both the reaction rate and K-factor are increased by practice with a mixed solvent according to the invention, in comparison to practice with a 1,4-butanediol solvent. At a pressure of about 910 psig, practice with a mixed solvent under the invention does not increase reaction rate over that attained with the 1,4-butanediol solvent, but does result in a significantly higher K-factor. At the relatively low pressure of about 720 psig, not according to the invention, there is no significant difference between the use of a mixed alkanol/diol solvent and the use of a diol solvent alone.

TABLE 4

| Solvent | | Pressure (psig) | Maximum reaction rate | K-factor[4] |
| --- | --- | --- | --- | --- |
| | 100% w 1,4-BD | 1310–1335 | 371 | 0.72 |
| 24% w, n-B | 76% w 1,4-BD | 1310–1335 | 470 | 0.83 |
| | 100% w 1,4-BD | 910 | 370 | 0.65 |
| 24% w, n-B | 76% w 1,4-BD | 910 | 301 | 0.735 |
| | 100% w 1,4-BD | 710–730 | 304[5] | 0.69 |
| 24% w, n-B | 76% w 1,4-BD | 710–730 | 271 | 0.70 |

[4] K-factor determined after 60 g ethylene uptake.
[5] Result of one experiment.

EXAMPLES 10-11

Table 5 presents the results of Examples 10 and 11, together with results of comparative experiment K, all run at a temperature of 95° C. and at pressures in the range from about 885–900 psig.

Example 11 illustrates the use of tertiary butanol (t-B) as the alkanol solvent component. A comparison of results of the three runs shows that practice with tertiary alkanol containing solvent mixture does not increase reaction rate but does increase K-factor, relative to the use of the 1,4-butanediol alone.

TABLE 5

| | Solvent[1] | | Maximum | K-factor | |
| --- | --- | --- | --- | --- | --- |
| | Alkanol | Diol | Reaction Rate | Intermediate[2] | Final[3] |
| Example No. | | | | | |
| 10 | 24% w n-B | 76% w 1,4-BD | 425 | 0.76 | 0.70 |
| 11 | 24% w t-B | 76% w 1,4-BD | 237 | 0.70 | |
| Comparative Experiment | | | | | |
| K | | 100% w 1,4-BD | 389 | 0.63 | |

I claim as my invention:

1. In a process for the preparation of oligomers of ethylene which comprises reacting ethylene in a polar solvent and in the presence of a catalyst which is a chelate of nickel with a bidentate ligand, the improvement which comprises reacting the ethylene under a partial pressure of ethylene of at least about 800 psig in a solvent mixture which comprises between about 40 and 82 percent by weight of one or more lower aliphatic dihydric alcohols and between about 18 to 60 percent by weight of one or more lower aliphatic monohydric alcohols, said percentages by weight being calculated on the total weight of the one or more lower aliphatic dihydric alcohols and the lower aliphatic monohydric alcohols in the solvent mixture.

2. The process of claim 1, wherein the one or more lower aliphatic dihydric alcohols are $C_2$ to $C_7$ aliphatic dihydric alcohols and the one or more lower aliphatic monohydric alcohols are $C_2$ to $C_7$ aliphatic monohydric alcohols.

3. The process of claim 2, wherein the ethylene is reacted at a temperature of at least about 80° C.

4. The process of claim 3, wherein the one or more aliphatic monohydric alcohols are primary or secondary alcohols.

5. The process of claim 4, wherein the one or more aliphatic dihydric alcohols are alpha-omega dihydric alcohols of four to six carbon atoms.

6. The process of claim 5, wherein the partial pressure of ethylene is in the range from about 900 to 2000 psig.

7. The process of claim 6, wherein ethylene is reacted at a temperature of at least about 85° C.

8. The process of claim 7, wherein the one or more aliphatic monohydric alcohols are selected from the group consisting of n-propanol, n-butanol and n-pentanol.

9. The process of claim 8, wherein 1,4-butanediol is the aliphatic dihydric alcohol.

10. The process of claim 9, wherein the partial pressure of ethylene is in the range from about 1000 to 1800 psig.

11. The process of claim 10, wherein the partial pressure of ethylene is in the range from about 1100 to 1500 psig.

12. The process of claim 3, wherein the partial pressure of ethylene is in the range from about 1100 to 1500 psig.

13. The process of claim 1, wherein the solvent mixture comprises between about 20 and 45 percent by weight of the one or more aliphatic monohydric alcohols and between about 55 and 80 percent by weight of the one or more aliphatic dihydric alcohols.

14. The process of claim 3, wherein the solvent mixture comprises between about 20 and 45 percent by weight of the one or more aliphatic monohydric alcohols and between about 55 and 80 percent by weight of the one or more aliphatic dihydric alcohols.

15. The process of claim 6, wherein the solvent mixture comprises between 20 and 40 percent by weight of the one or more aliphatic monohydric alcohols and between about 60 and 80 percent by weight of the one or more aliphatic dihydric alcohols.

16. The process of claim 3, wherein the solvent mixture comprises between about 35 and 60 percent by weight of the one or more aliphatic monohydric alcohols and between about 40 and 65 percent by weight of the one or more aliphatic dihydric alcohols.

17. The process of claim 1, wherein the solvent mixture comprises between about 20 and 35 percent by weight of the one or more aliphatic monohydric alcohols and between about 65 and 80 percent by weight of the one or more aliphatic dihydric alcohols.

18. The process of claim 3, wherein the solvent mixture comprises between about 20 and 35 percent by weight of the one or more aliphatic monohydric alcohols and between about 65 and 80 percent by weight of the one or more aliphatic dihydric alcohols.

19. The process of claim 6, wherein the solvent mixture comprises between about 20 and 35 percent by weight of the one or more aliphatic monohydric alcohols and between about 65 and 80 percent by weight of the one or more aliphatic dihydric alcohols.

20. In a process for the preparation of oligomers of ethylene which comprises reacting ethylene in a solvent and in the presence of a catalyst which is a chelate of nickel with a bidentate ligand, the improvement which comprises reacting the ethylene at a temperature of at least about 85° C. and under a partial pressure of ethylene between about 1100 and 1500 psig in a solvent mixture which comprises between about 60 and 80 percent by weight of 1,4-butanediol and between about 20 and 40 percent by weight of one or more alcohols selected from the group consisting of n-propanol and n-butanol, said percentages by weight being calculated on the total weight of 1,4-butanediol, n-propanol and n-butanol in the solvent mixture.

21. The process of claim 1, wherein the ligand is an o-dihydrocarbylphosphinobenzoic acid or an alkali metal salt thereof.

22. The process of claim 21, wherein the ligand is o-diphenylphosphinobenzoic acid or an alkali metal salt thereof.

23. The process of claim 6, wherein the ligand is an o-dihydrocarbylphosphinobenzoic acid or an alkali metal salt thereof.

24. The process of claim 23, wherein the ligand is o-diphenylphosphinobenzoic acid or an alkali metal salt thereof.

25. The process of claim 15, wherein the ligand is an o-dihydrocarbylphosphinobenzoic acid or an alkali metal salt thereof.

26. The process of claim 25, wherein the ligand is o-diphenylphosphinobenzoic acid or an alkali metal salt thereof.

27. The process of claim 20, wherein the ligand is an o-dihydrocarbylphosphinobenzoic acid or an alkali metal salt thereof.

28. The process of claim 27, wherein the ligand is o-diphenylphosphinobenzoic acid or an alkali metal salt thereof.

* * * * *